United States Patent
Villen Altamirano et al.

(10) Patent No.: US 7,695,617 B2
(45) Date of Patent: Apr. 13, 2010

(54) INTERPHASE INJECTOR DEVICE FOR THE DIRECT COUPLING OF LIQUID CHROMATOGRAPHY AND GAS CHROMATOGRAPHY

(75) Inventors: Jesus Villen Altamirano, Albacete (ES); Ana Maria Vazquez Molini, Albacete (ES); Raquel Sanchez Santiago, Albacete (ES); Rouger Gilbert Fortuny, Albacete (ES)

(73) Assignee: Universidad de Gastill-la Mancha, Albacete (ES)

( * ) Notice: Subject to any disclaimer, the term of this patent is extended or adjusted under 35 U.S.C. 154(b) by 0 days.

(21) Appl. No.: 11/915,012

(22) PCT Filed: Mar. 30, 2006

(86) PCT No.: PCT/ES2006/000154

§ 371 (c)(1),
(2), (4) Date: Mar. 28, 2008

(87) PCT Pub. No.: WO2006/122993

PCT Pub. Date: Nov. 23, 2006

(65) Prior Publication Data

US 2008/0272044 A1    Nov. 6, 2008

(30) Foreign Application Priority Data

May 20, 2005 (ES) ............................... 200501284

(51) Int. Cl.
*B01D 15/08* (2006.01)
*B01D 53/14* (2006.01)
*C02F 1/28* (2006.01)
*B01D 53/02* (2006.01)

(52) U.S. Cl. ...................... 210/198.2; 210/656; 96/101; 96/105; 96/106

(58) Field of Classification Search .............. 210/198.2, 210/656; 95/89; 96/101, 105, 106
See application file for complete search history.

(56) References Cited

U.S. PATENT DOCUMENTS 3,258,467 A    6/1966   Jacobsen (Continued)

FOREIGN PATENT DOCUMENTS

WO    9961127    12/1999

OTHER PUBLICATIONS

International Preliminary Report on Patentability dated Nov. 28, 2007 from the corresponding PCT/ES2006/000154.

(Continued)

*Primary Examiner*—Krishnan S Menon
*Assistant Examiner*—Katherine Zalasky
(74) *Attorney, Agent, or Firm*—Katten Muchin Rosenman LLP

(57) ABSTRACT

The invention relates to an interface injector device for the direct coupling of liquid chromatography and gas chromatography, comprising an outer body (1) with an inner cavity with two inner chambers (2a, 2b) separated by a dividing element (9, 11a); a first passage (3) of the first chamber (2a) to a waste duct (8); an inner tube (5) arranged in the inner cavity and traversing the dividing element (9, 11a), and having a first section (5a) in the first inner chamber (2a), a second section (5b) in the second inner chamber (2b), and an inner channel (5f) which can house an adsorbent material (6), and at least one inorganic wool material (7) retained in the first section (5a) of the inner tube by retaining means (7), a first opening (10) communicated with the waste duct (8) exclusively through the first inner chamber (2a).

12 Claims, 4 Drawing Sheets

U.S. PATENT DOCUMENTS

| | | | |
|---|---|---|---|
| 3,810,545 | A | 5/1974 | Rasmussen et al. |
| 4,793,920 | A | 12/1988 | Cortes et al. |
| 5,223,435 | A * | 6/1993 | Kohr ........................ 210/198.2 |
| 5,347,844 | A * | 9/1994 | Grob et al. .................. 73/23.41 |
| 5,800,692 | A * | 9/1998 | Naylor et al. ............... 204/601 |
| 6,223,584 | B1 | 5/2001 | Mustacich et al. |
| 6,311,544 | B1 * | 11/2001 | Bertrand .................. 210/198.2 |
| 6,402,947 | B1 | 6/2002 | Altamirano et al. |
| 2005/0032230 | A1 | 2/2005 | Jalil |

OTHER PUBLICATIONS

Supplementary European Search Report and Annex to the European Search Report, dated Jan. 13, 2009 for corresponding European Application EP 06 74 3416.

M.Perez, et al., "On-line reversed phase LG-GC by using the new TOTAD (through oven transfer adsorption desorption) interface: application to parathion residue analysis", Journal of Microcolumn Separations, 1999, pp. 582-589, vol. 11.

M.Perez, et al., "Pesticide residue analysis by off-line, SPE and on-line reversed-phase LC-GC using the through-oven-transfer adsorption/desorption interface", Analytical Chemistry, 2000, pp. 846-852, vol. 72, American Chemical Society.

R. Sanchez, et al., "Automated multiresidue analysis of pesticides in olive oil by on-line reversed phase liquid chromatography—gas chromatography using the through oven transfer adsorption-desorption interface",2004, pp. 167-172, Journal of Chromatography.

Konrad Grob; Development of the Transfer Techniques for On-line High-performance Liquid Chromatography-Capillary Gas Chromatography; Journal of Chromatography A, 703 (1995) 265-276; Elsevier Science B.V.

Luigi Mondello, Giovanni Dugo, Keith D. Bartle; On-line Microbore High Performance Liquid Chromatography-Capillary Gas Chromatography For Food and Water Analyses. A Review; J. Microcolumn Separations, 8(4) 275-310 (1996); John Wiley & Sons, Inc.

F.J. Senorans, J. Villen, J. Tabera, and M. Herraiz; Simplex Optimization of the Direct Analysis of Free Sterols in Sunflower Oil by On-line Coupled Reversed Phase Liquid Chromatography-Gas Chromatography; J. Agric. Food Chem. 1998, 46, 1022-1026; American Chemical Society 1998.

Gracia P. Blanch, Jesus Villen, and Marta Herraiz; Rapid Analysis of Free Erythrodiol and Uvaol in Olive Oils by Coupled Reversed Phase Liquid Chromatography—Gas Chromatography; J. Agric. Food Chem. 1998, 46, 1027-1030; American Chemical Society 1998.

Jolan J. Vreuls, Gerhardus J. De Jong, Rudi T. Ghijsen, and Udo A. TH. Brinkman; Liquid Chromatography Coupled On-Line with Gas Chromatography: State of the Art; Journal of AOAC International vol. 77, No. 2, 1994.

International Search Report dated Aug. 17, 2006, for corresponding International Application PCT/ES2006/000154.

M. Perez et al.; "Pesticide Residue Analysis by Off-Line SPE and On-Line Reversed-Phase LC-GC Using the Throug-Oven-Transfer Adsorption/Desorption Interface"; Analytical Chemistry; vol. 72; No. 4; Feb. 15, 2000; pp. 846-852.

R. Sanchez et al.; "Direct Analysis of Pesticide Residues in Olive Oil by On-Line Reversed Phase Liquid Chromatography-Gas Chromatography Using an Automated Through Oven Transfer Adsorption Desorption (TOTAD) Interface"; Journal of Agricultural and Food Chemistry; vol. 51; (2003); pp. 6098-6102.

R. Sanchez et al.; "Determination of Organophosphorus and Triazine Pesticides in Olive Oil by On-Line Coupling Reversed-Phase Liquid Chromatography/Gas Chromatography with Nitrogen-Phosphorus Detection and an Automated Through-Oven Transfer Adsorption-Desorption Interface"; Journal of AOAC International; vol. 88; No. 4; (2005); pp. 1255-1250.

J. Hinshaw et al.; "Introduction to Open-Tubular Column Gas Chromatography"; Produced in Conjunction with LC-GC Magazine; pp. 1-2.

Jose Luis Perez Pavon et al.; "Use of a programmed temperature vaporizer and an in situ derivatization reaction to improve sensitivity in headspace-gas chromatography. Application to the analysis of chlorophenols in water"; Journal of Chromatography A.; Elsevier; vol. 1216; (2009); pp. 1192-1199.

Jose M. Cortez et al.; "Large Volume GC Injection for the Analysis of Organophosphorus Pesticides in Vegetables Using the Through Oven Transfer Adsorption Desorption (TOTAD) Interface"; Journal of Agricultural and Food Chemistry; vol. 54; (2006); pp. 1997-2002.

K. Grob; "Classical Split and Splitless Injection in Capillary Gas Chromatography with some remarks on PTV injection"; Hethig Verlag, New York;(1988); pp. 32-33.

P. Sandra; "Sample Introduction in Capillary Gas Chromatography"; vol. 1; Hethig Verlag, New York;(1985); p. 8.

* cited by examiner

INTERPHASE INJECTOR DEVICE FOR THE DIRECT COUPLING OF LIQUID CHROMATOGRAPHY AND GAS CHROMATOGRAPHY

TECHNICAL FIELD OF THE INVENTION

The present invention belongs to the field of instrumental analysis systems in analytical chemistry, and specifically, to the field of devices allowing to directly couple liquid chromatography and gas chromatography.

PRIOR STATE OF THE ART

The use of a direct coupling of high performance liquid chromatography and gas chromatography is very useful for analyzing complex mixtures. The advantages in using this multidimensional system basically centre on the possibility of combining the liquid chromatography potential as a sample preparation technique with that of gas chromatography in relation to the system's performance (Grob, K On-Line Coupled LC-GC. Hüthig, Heidelberg, Germany, 1991; Mondello, L.; Dugo, G.; Bartle, K D. J. Microcol. September 1996, 8, 275-310). It is therefore possible to avail of analysis methods which do not require the use of conventional sample preparation processes which, apart from being laborious and unreliable, have the drawback of calling for the use of relatively high volumes of polluting organic solvents.

A particularly problematic aspect in connection with the use of direct coupling of liquid chromatography and gas chromatography relates to the characteristics of the interface necessary to make this coupling possible. This is an aspect which displays the difficulty in making two essentially different systems, in which the operating parameters are substantially different, compatible. The interfaces initially developed only allowed the use of a normal phase in the pre-separation performed by liquids since, in this case, the small volumes of vaporization produced during the transfer do not lead to any additional difficulties. This is why different interfaces (autosampler, on-column, loop type) enabling direct coupling to be carried out between liquid chromatography in the normal phase and gas chromatography (Grob, K. J. Chromatogr. A 1995, 703, 265-76; Vreuls, J. J.; de Jong, G. J.; Ghijsen, R. T.; Brinkman, U. A. Th. J. AOAC. Int. 1994, 77, 306-27) have been designed and used.

However, it is necessary in many cases to turn to the use of the reverse phase in the liquid chromatography stage in order to achieve a certain separation and, consequently, the extension of the field of applicability of direct liquid chromatography and gas chromatography coupling requires the development of suitable interfaces for carrying out direct coupling between liquid chromatography in a reverse phase and gas chromatography (Señsorans, F. J.; Villén, J; Tabera, J.; Herraiz, M. J. Agric. Food Chem. 1998, 46, 1028-27. Villén, J; Blanch, G. P.; Ruiz of the Castillo, M. L.; Herraiz, M. J. Agric. Food Chem. 1998, 46, 1027-31). With this aim in mind, several systems (retention gap, concurrent solvent evaporation, open tubular trap, etc) have been proposed over the last few years (Grob, K. J. Chromatogr. A 1995, 703, 265-76; Vreuls, J. J.; de Jong, G. J.; Ghijsen, R. T.; Brinkman, U. A. Th. J. AOAC. Int. 1994, 77, 306-27) although the limitations involved in using polar eluents (fundamentally the high volumes of vaporization produced during transfer and the difficulty of suitably focusing the chromatographic band) have prevented the development of interfaces meeting the required conditions as regards simplicity, reliability, versatility and possibility of automation.

Patent application WO99/061127, corresponding to US patent document 6402947-B1, the content of which is herein included by reference, describes an interface device for the direct coupling of liquid chromatography and gas chromatography, designed based on a basic scheme of a PTV (programmed temperature vaporizer) injector which has been modified so that is can be used for the direct coupling of liquid chromatography in normal phase or reverse phase, and gas chromatography and for the introduction of high volumes in gas chromatography. This interface device comprises an outer body with a first end part, a second end part, an intermediate section between said end parts, and an inner cavity divided into a first inner chamber and a second inner chamber, as well as an inner tube arranged in said inner cavity. The inner tube has a first section arranged in the first inner chamber, a second section arranged in the second inner chamber, the first section ending in a first end with a first opening and the second section ending in a second end, as well as an inner channel for housing an adsorbent material trapped between two "plugs" of inorganic wool material, such as for example glass wool. The first section of the inner tube is communicated with a waste duct. The injector body also comprises a dividing element surrounding the inner tube and dividing the inner cavity into the first inner chamber and the second inner chamber. The device further comprises a system for selecting a liquid chromatography fraction and leading it to the inner tube by means of a first duct penetrating into the tube through its free end and a first valve connected to the opposite end of the first duct, and a discharge system for discharging the liquid chromatography fraction into the inner tube.

This discharge system is designed to prevent the liquid chromatography fraction from entering the gas chromatography column when the device operates in the adsorption mode. To that end, the free end of the first duct ends inside the inner tube and a second duct communicated with the gas chromatography column penetrates into the inner tube beyond the first duct, such that it ends closer to the adsorbent material than the free end of the first duct. Likewise, the discharge system comprises a first gas inlet for the entry of a pressurized gas to the first inner chamber of the outer body and a solvent evacuation system comprising an outlet valve connected to a waste tube, which outlet valve is closed when the system operates in the desorption mode and open when the system operates in the adsorption mode, as well as a hydraulic system for gases comprising pressure reducing devices, opening and closing devices and flow controlling valves connected to the mentioned first gas inlet, to the second gas inlet and to a gas tank containing pressurized gas for supplying the aforementioned pressurized gas flow.

It has been verified that the interface injector device described in document WO99/061127 has a series of drawbacks, although it allows effectively changing, by means of the direct coupling of liquid chromatography and gas chromatography, operating in an adsorption mode and in a desorption mode. Thus, firstly, during the adsorption step when the outlet valve connected to the waste tube is open, an overpressure occurs in the first chamber due to a gradual obstruction of the waste tube by the pieces of inorganic wool material swept along by the vaporized solvent flow and the gas flow, this overpressure causing a drastic decrease in the analysis sensitivity. These pieces of inorganic wool material come from its friction with the end of the tube housed in the "plug" of said material between the adsorbent material and the first opening in the first end of the inner tube. On the other hand, the detachment of these pieces of inorganic wool material also leads to the progressive obstruction of the mentioned outlet valve and the corresponding malfunctions.

DESCRIPTION OF THE INVENTION

The object of the present invention is to overcome the aforementioned drawbacks by means of an interface injector device for the direct coupling of liquid chromatography and gas chromatography which can work in an adsorption mode and in a desorption mode, comprising an outer body with a first end part, a second end part, an intermediate section between said end parts, and an inner cavity in which there is a first inner chamber and a second inner chamber;

at least one first passage from the first chamber to a waste tube, and at least one second passage from the second chamber to the outside of the injector body;

an inner tube arranged in said inner cavity;

a dividing element surrounding the inner tube, and dividing the inner cavity into said first inner chamber and said second inner chamber;

the inner tube having a first section arranged in the first inner chamber, a second section arranged in the second inner chamber, the first section ending in a first end with a first opening and the second section ending in a second end with a second opening, an inner channel extending between said first and said second opening, said channel being able to house at least one adsorbent material, and at least one inorganic wool material arranged in the first section of the inner tube, and the first section of the inner tube being communicated with a waste duct;

wherein the first end of the inner tube has retaining means for retaining the inorganic wool material, the first opening of the inner tube communicates with the first passage to the waste tube exclusively through the first inner chamber.

This structure allows retaining the "plug" of inorganic wool material, such as glass wool, without needing a contact with the waste tube; therefore there is no friction between said tube and said material. On the other hand, the fact that the first inner chamber is placed between the first passage to the waste tube and the first opening of the inner tube implies that, since the waste tube can have the same diameter as said chamber, the pieces of said material cannot obstruct the waste tube or the outlet valve arranged in said tube.

According to the invention, the retaining means can be an occluding partition in which said first opening is placed, said first opening having a diameter smaller than the diameter of the inner tube, or such means can be formed as a progressive narrowing of the inner volume of the first end in a direction towards said first opening, said first opening being defined at the end of the narrowing, for example by means of a frusto-conical inner configuration of the first end of the inner tube.

In one embodiment of the invention, the dividing element and the first inner chamber are defined by a detachable element that is immobilized in said first end part of the injector body. According to another embodiment of the invention, the dividing element can in turn be defined by a first detachable element and the first inner chamber can be defined in a second detachable element, said first and said second detachable element being in contact and immobilized in said first end part of the injector body. The dividing element can be a ring-shaped element with a first bevel edge for example and the second detachable element can be a cylindrical element with a second bevel edge, said bevel edges having complementary configurations such that they make contact in a shape attachment.

According to the invention, the interface injector device can comprise a first gas inlet to the first inner chamber and/or a second gas inlet to the second inner chamber. The device can also comprise a first duct which can be connected to a gas chromatography device, and a second duct which can be connected to a liquid chromatography device, said ducts penetrating into the inner channel in the second section of the inner tube through the second end of the inner tube. The second duct preferably penetrates into said channel at a greater depth than the first duct.

The inner tube is preferable made of an inert material, such as glass for example.

It can be observed that the present invention effectively solves the drawbacks of interface injector devices by means of a simple and inexpensive structure, and at the same time it can be incorporated to the system described in patent application WO99/061127 without needing substantial structural changes.

BRIEF DESCRIPTION OF THE DRAWINGS

Several embodiments of the invention will be described below based on figures in which.

Figure 1:
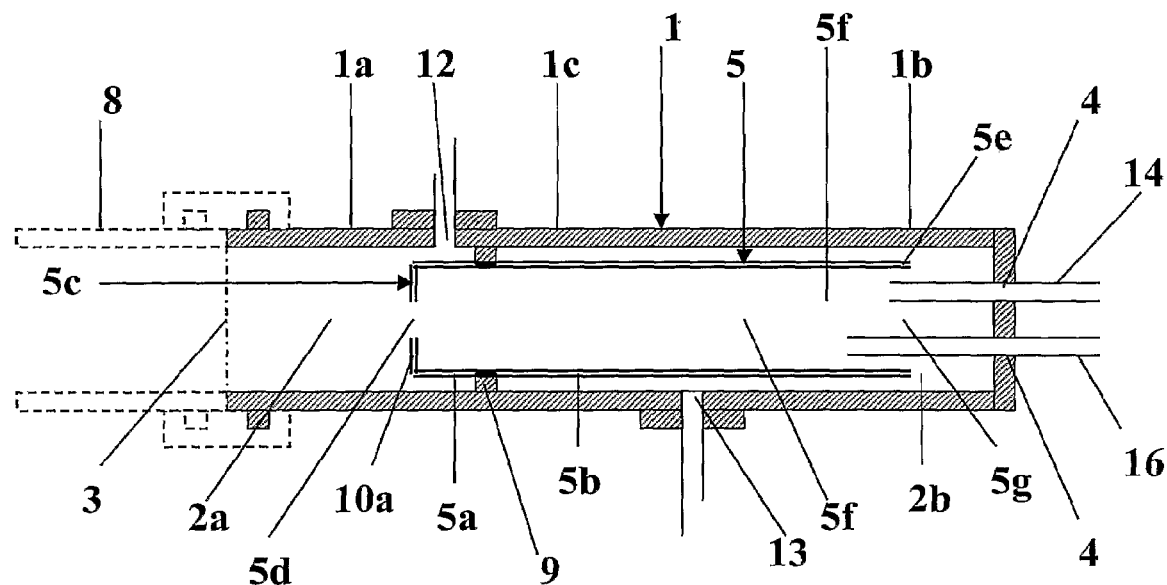
FIG. 1 shows a side sectional view of a first embodiment of the invention.

In these figures there are numerical references identifying the following elements:

1 injector body
1a first end part,
1b second end part
1c intermediate section
2a first inner chamber
2b second inner chamber
3 first passage from the first chamber to the outside
4 second passage from the second chamber to the outside
5 inner tube arranged in the inner cavity
5a first section
5b second section
5c first end
5d first opening
5e second end
5f inner channel
5g second opening
6 adsorbent material
7 inorganic wool material
8 waste duct
9 dividing element
10a occluding partition
10b narrowing
11 detachable element immobilized in said first end part of the injector body.
11a first detachable element
11b second detachable element
11c first bevel edge
11d second bevel edge 12 first gas inlet to the first inner chamber
12a inlet in the outer body
12b ring-shaped chamber
13 second gas inlet to the second inner chamber
14 first duct
15 gas chromatography device
16 second duct
17 liquid chromatography device
18 first waste tank
19 second waste tank
20 gas chromatography oven
21 multiple-way valve
22 inert gas tank
23 first electrically-operated valve
24 second electrically-operated valve
25 third electrically-operated valve
26 first controlling device with a pressure regulator and a flow regulator
27 second controlling device with a pressure regulator and a flow regulator

EMBODIMENTS OF THE INVENTION

FIG. 1 shows a first embodiment of the device of the present invention, comprising an outer body 1 with a first end part 1a, a second end part 1b and an intermediate section 1c between said end parts 1a,1b. The body 1 internally has a cavity divided into first inner chamber 2a and a second inner chamber 2b. The first chamber has a first passage 3 to the outside of the device, connected to a waste duct 8. The second chamber in turn has two passages 4 to the outside. In the inner cavity, there is arranged an inner tube 5 surrounded by a dividing partition 9 surrounding the inner tube and dividing the inner cavity into the first inner chamber 2a and the second inner chamber 2b.

The inner tube 5, made of inert glass which is conventional in itself, comprises a first section 5a arranged in the first inner chamber 2a, a second section 5b arranged in the second inner chamber 2b. The first section 5a of the inner tube is finished in a first end 5c with an opening 5d, whereas its second section 5b is finished in a second end 5e with a second opening 5g. An inner channel 5f extends between the first and the second opening 5d, 5e, which channel, as can be seen in FIG. 2, can house an adsorbent material 6 which is conventional in itself (such as TENAX TA for example) and is trapped between two "plugs" of an inorganic wool material 7 such as glass fiber for example.

The first end 5c of the inner tube 5 has retaining means in the form of an occluding partition 10a retaining the inorganic wool material, and in which there is the first opening 5d, such that the first opening 5d of the inner tube 5 communicates with the first passage 3 exclusively through the inner chamber 2a.

Figure 2:
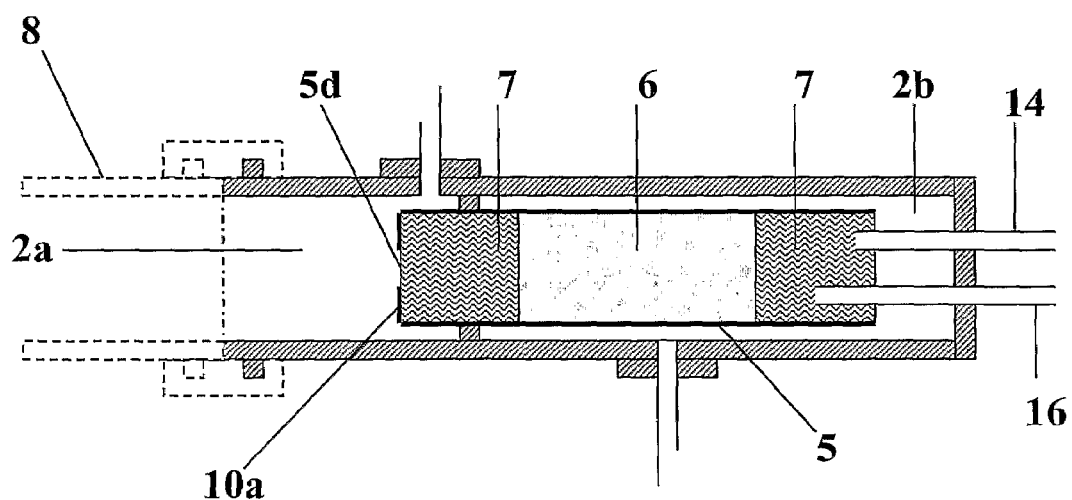
FIG. 2 shows a side sectional view corresponding to FIG. 1, but in which the inner tube is filled with an adsorbent material retained between two "plugs" of inorganic wool.

The interface injector device shown in FIGS. 1 and 2 further comprises a first gas inlet 12 to the first inner chamber 2a, and a second gas inlet 13 to the second inner chamber 2b.

The device also has a first duct 14 traversing one of the passages 4 in the second end of the outer body, for its connection to a gas chromatography device (not shown in FIGS. 1 to 5), and a second duct 16 traversing the other passage 4 for its connection to the liquid chromatography device (not shown in FIGS. 1 to 5). The ducts 14,16 penetrate into the inner channel 5f of the inner tube 5 through the second end 5e of the tube. The second duct 16 penetrates into said channel 5f at a greater depth than the first duct 14.

Figure 3:
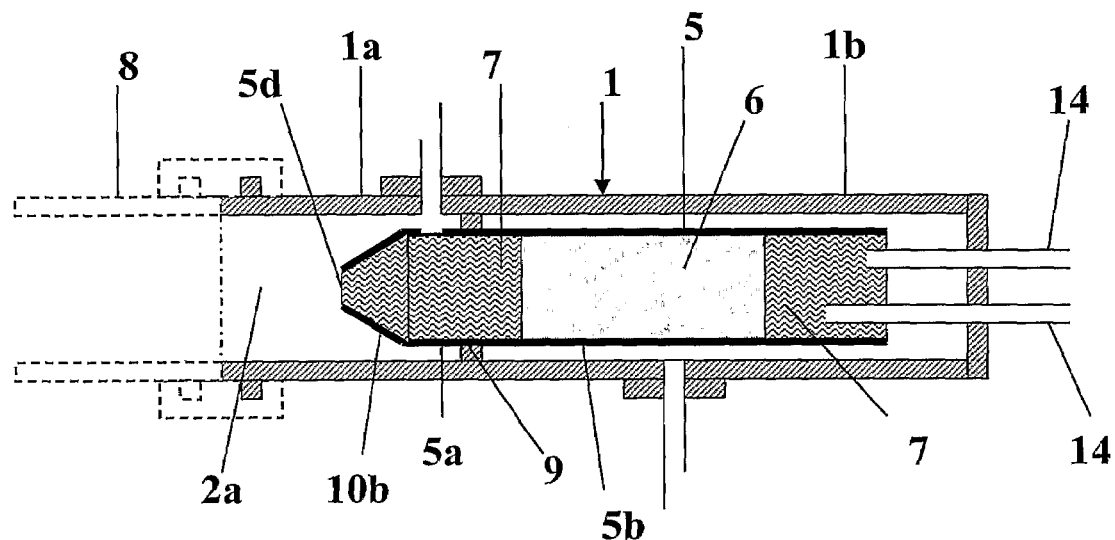
FIG. 3 shows a side sectional view of a second embodiment of the invention.

The second embodiment of the invention shown in FIG. 3 is only different from the first embodiment shown in FIGS. 1 and 2 in that the retaining means can be formed by a progressive narrowing 10b of the inner volume of the first end 5c of the tube 5 in a direction towards the first opening 5d of the tube 5, such that this first opening 5d is defined at the end of the narrowing 10b which has a frustoconical inner configuration in the embodiment shown in FIG. 3.

Figure 4:
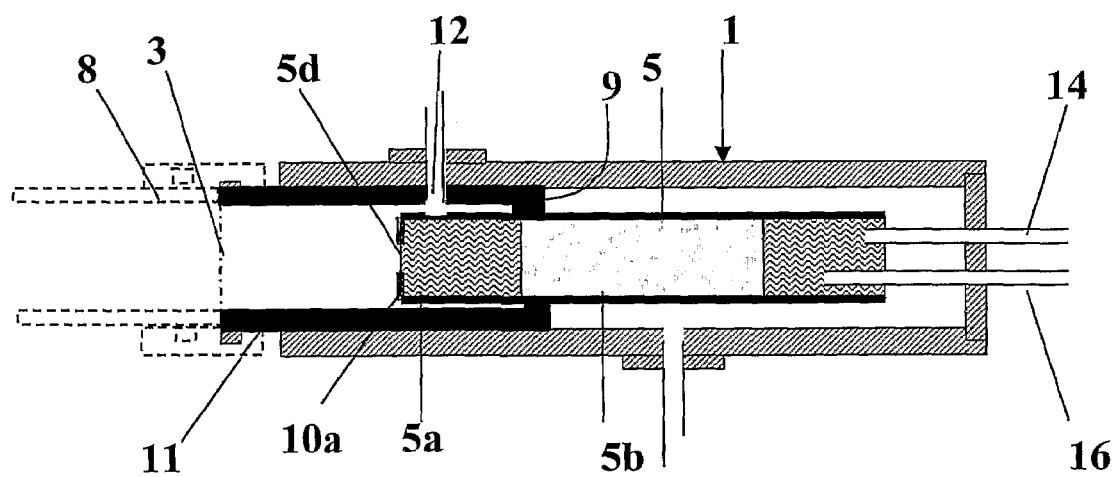
FIG. 4 shows a side sectional view of a third embodiment of the invention.

In the third embodiment of the invention shown in FIG. 4, the dividing element 9 and the first inner chamber 2a are defined by a cylindrical detachable element 11 which is immobilized in the first end part 1a of the outer body 1. In this embodiment, the first gas inlet 12 penetrates through the outer body 1 and the detachable element 11. The waste tube 8 is directly connected to the open end of the detachable element 11 defining the passage 3 from the first chamber 2a to the outside.

Figure 5:
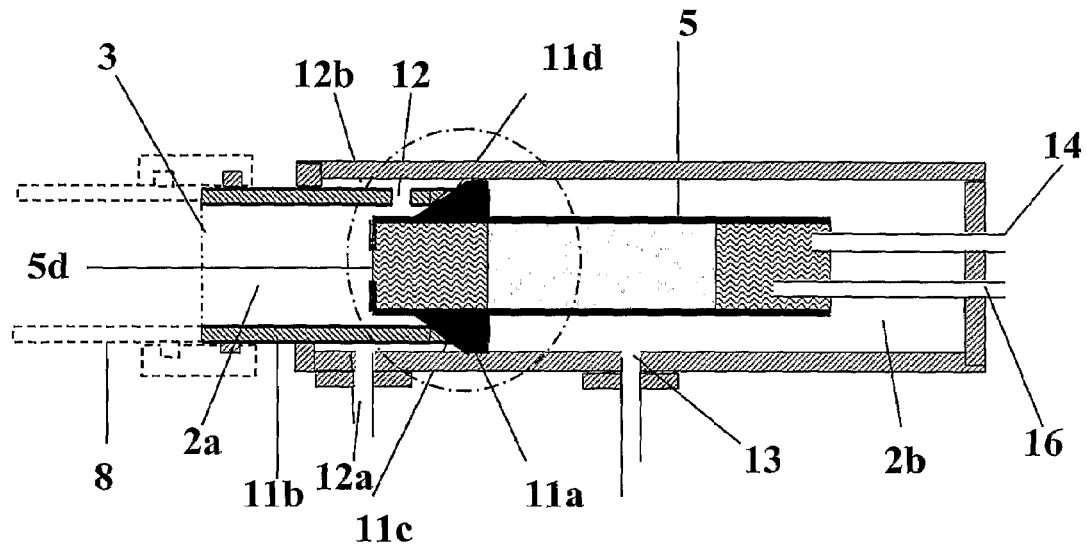
FIG. 5 shows a side sectional view of a fourth embodiment of the invention.
Figure 6:
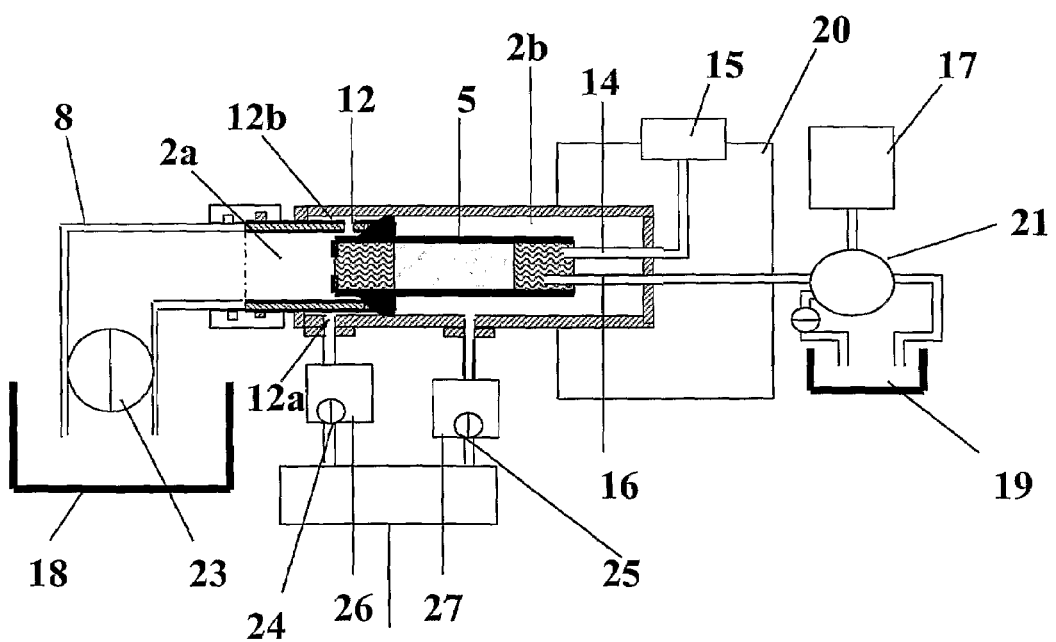
FIG. 6 shows a side sectional view of the fourth embodiment of the invention incorporated to a system for the direct coupling of liquid chromatography and gas chromatography.
Figure 7:
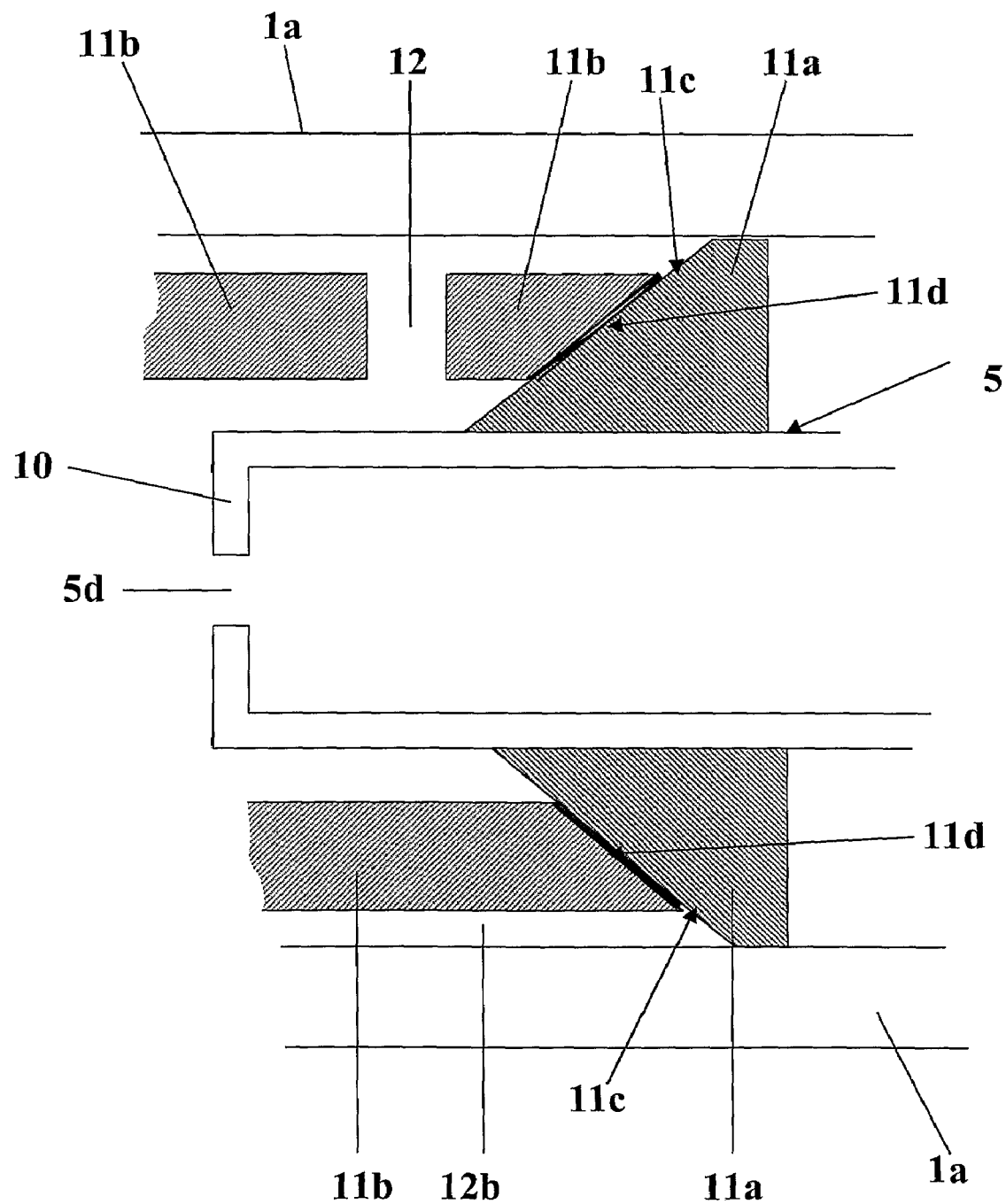
FIG. 7 shows a view of the area marked with a dash-dot line in FIG. 5.

In the fourth embodiment of the invention shown in FIGS. 5 and 7, the device comprises two detachable elements 11a, 11b. In the shown embodiment, the first detachable element 11a is a ring-shaped element provided with a first bevel edge 11c and forms the dividing element separating the first chamber 2a from the second chamber. The second detachable element 11b is in turn a cylindrical body inside which the first chamber 2a is defined, and which has a second bevel edge 11d complementary to the first bevel edge 11c at one of its end edges. The first detachable element 11a and the second detachable element 11b, make contact and are immobilized in the first end part of the outer body 1a. The bevel edges 11c, 11d have complementary configurations such that they make contact in a shape attachment. The gas inlet 12 to the chamber interior 2a is communicated with the inlet in the injector body 12a through a ring-shaped space 12b.

An inert gas tank 22, of helium for example, is connected to the gas inlet 12 of the first chamber 2a through the inlet 12a and the ring-shaped space 12b. A second electrically-operated opening and closing valve 24, as well as a first controlling device 26 with a pressure regulator and a flow regulator, are placed in the connecting duct between the inlet 12a and the gas tank 22. In turn, the waste tank can also be connected through a third electrically-operated opening and closing valve 25 with a second controlling device 27 with a pressure regulator and a flow regulator, to the second inlet 13 communicating with the second inner chamber 2b.

The first duct 14 emerging from the second chamber 2b is connected to a gas chromatography device 15 comprising an oven 20, whereas the second duct 16 is selectively connected to a liquid chromatography device 17 and to a second waste tank 19 through a multiple-way valve.

The invention claimed is:
1. An interface injector device for the direct coupling of liquid chromatography and gas chromatography, which can work in an adsorption mode and in a desorption mode, comprising
   an outer body (1) with a first end part (1a), a second end part (1b), an intermediate section (1c) between said end parts (1a,1b), and an inner cavity in which there is a first inner chamber (2a) and a second inner chamber (2b);
   at least one first passage (3) from the first chamber (2a) to a waste duct (8), and at least one second passage (4) from the second chamber (2b) to the outside of the injector body;
   an inner tube (5) arranged in said inner cavity;
   a dividing element (9,11a) surrounding the inner tube (5) and separating said first inner chamber (2a) from said second inner chamber (2b);
   the inner tube (5) having
   a first section (5a) arranged in the first inner chamber (2a), a second section (5b) arranged in the second inner cham- ber (2*b*), the first section (5*a*) ending in a first end (5*c*) with a first opening (5*d*) and the second section (5*b*) ending in a second end (5*e*) with a second opening (5*g*);

an inner channel (5*f*) extending between said first and said second opening (5*d*,5*g*), said channel (5*f*) being able to house at least one adsorbent material (6), and at least one inorganic wool material (7) arranged in the first section (5*a*) of the inner tube;

characterized in that the first end (5*c*) of the inner tube (5) has retaining means (10*a*,10*b*) for retaining the inorganic wool material (7), the first opening (5*d*) of the inner tube (5) communicates with the first passage (3) to the waste duct (8) exclusively though the first inner chamber (2*a*).

2. An interface injector device according to claim 1, characterized in that said retaining means are an occluding partition (10*a*) in which said first opening (5*d*) is placed, said first opening (5*d*) having a diameter smaller than the inner diameter of the inner tube (5).

3. An interface injector device according to claim 1, characterized in that the retaining means are defined by a narrowing (10*b*) of the inner volume of the first end (5*c*) of the tube (5) which narrows progressively in the direction towards said first opening (5*d*), said first opening (5*d*) being defined at the end of the narrowing (10*b*).

4. An interface injector device according to claim 3, characterized in that the first end (5*c*) of the inner tube has a frustoconical inner configuration.

5. An interface injector device according to claim 1, characterized in that the dividing element (9) and the first inner chamber (2*a*) are defined by a detachable element (11) immobilized in said first end part (1*a*) of the outer body (1) of the interface injector device.

6. An interface injector device according to claim 1, characterized in that the dividing element is defined by a first detachable element (11*a*) and the first inner chamber (2*a*) is defined in a second detachable element (11*b*), said first and said second detachable elements (11*a*,11*b*) making contact and being immobilized in said first end part (1*a*) of the outer body (1).

7. An interface injector device according to claim 6, characterized in that the first detachable element (11*a*) is a ring-shaped element with a first bevel edge (11*c*) and the second detachable element (11*b*) is a cylindrical element with a second bevel edge (11*d*), said bevel edges (11*c*,11*d*) having complementary configurations such that they make contact in a shape attachment.

8. An interface injector device according to claim 1, characterized in that the inner tube (5) is made of glass.

9. An interface injector device according to claim 1, characterized in that it comprises a first gas inlet (12) to the first inner chamber (2*a*).

10. An interface injector device according to claim 1, characterized in that it comprises a second gas inlet (13) to the second inner chamber (2*b*).

11. An interface injector device according to claim 1, characterized in that it comprises a first duct (14) which can be connected to a gas chromatography device (15), and a second duct (16) which can be connected to a liquid chromatography device (17), said ducts (14,16) penetrating into the inner channel (5*f*) in the second section (5*b*) of the inner tube (5) though the second end (5*e*) of said inner tube (5).

12. An interface injector device according to claim 11, characterized in that the second duct (16) penetrates into said channel (5*f*) at a greater depth than the first duct (14).

* * * * *